(12) United States Patent
Gutierrez (10) Patent No.: US 6,855,674 B2
(45) Date of Patent: Feb. 15, 2005

(54) HYDROXY AROMATIC MANNICH BASE CONDENSATION PRODUCTS AND THE USE THEREOF AS SOOT DISPERSANTS IN LUBRICATING OIL COMPOSITIONS

(75) Inventor: Antonio Gutierrez, Mercerville, NJ (US)

(73) Assignee: Infineum International Ltd. (GB)

( * ) Notice: Subject to any disclaimer, the term of this patent is extended or adjusted under 35 U.S.C. 154(b) by 0 days.

(21) Appl. No.: 10/265,948

(22) Filed: Dec. 2, 2002

(65) Prior Publication Data

US 2003/0173251 A1 Sep. 18, 2003

Related U.S. Application Data

(63) Continuation-in-part of application No. 10/209,522, filed on Jul. 30, 2002, and a continuation-in-part of application No. 09/746,038, filed on Dec. 22, 2000, now Pat. No. 6,495,496.

(51) Int. Cl.$^7$ .................. C10M 133/48; C07D 265/12
(52) U.S. Cl. ..................... 508/246; 544/89; 544/90
(58) Field of Search ............... 544/89, 90; 508/246

(56) References Cited

U.S. PATENT DOCUMENTS

| | | | | |
|---|---|---|---|---|
| 2,407,044 A | | 9/1946 | Tyrer | 260/628 |
| 2,407,055 A | | 9/1946 | Bradner | 129/29 |
| 2,451,996 A | | 10/1948 | Tyrer | 260/628 |
| 2,459,112 A | | 1/1949 | Oberright | 252/51.5 |
| 2,806,031 A | * | 9/1957 | Rigterink | 544/90 |
| 2,861,991 A | * | 11/1958 | Rigterink | 544/90 |
| 3,033,903 A | | 5/1962 | Loeb | 260/621 |
| 3,082,112 A | * | 3/1963 | Hemwall | 106/287.21 |
| 3,087,936 A | | 4/1963 | Le Suer | 260/326.3 |
| 3,172,892 A | | 3/1965 | Le Suer | 260/326.5 |
| 3,215,707 A | | 11/1965 | Rense | 260/326.3 |
| 3,231,587 A | | 1/1966 | Rense | 260/346.8 |
| 3,254,025 A | | 5/1966 | Le Suer | 252/32.7 |
| 3,272,746 A | | 9/1966 | Le Suer et al. | 252/47.5 |
| 3,275,554 A | | 9/1966 | Wagenaar | 252/50 |
| 3,381,022 A | | 4/1968 | Le Suer | 260/404.8 |
| 3,442,808 A | | 5/1969 | Traise et al. | 252/49.6 |
| 3,458,495 A | | 7/1969 | Younghouse et al. | 260/136 |
| 3,539,633 A | | 11/1970 | Piasek et al. | 260/570.5 |
| 3,565,804 A | | 2/1971 | Honnen et al. | 252/50 |

(List continued on next page.)

FOREIGN PATENT DOCUMENTS

| | | | | |
|---|---|---|---|---|
| EP | 0 596 499 A1 | 5/1994 | | C10L/1/30 |
| EP | 208 560 B2 | 12/1998 | | C10M/129/93 |
| GB | 989409 | 4/1965 | | |
| GB | 1440219 | 6/1976 | | C08F/8/46 |
| WO | WO94/07842 | 4/1994 | | C07C/215/48 |

OTHER PUBLICATIONS

Database Crossfire Beilstein Online!, Beilstein Institut zur Forderung der Chemischen Wissenschaften, Frankfurt am Main, DE, Database accession No. 3924453, XP002215699 abstract, vol. 34, No. 35, 1993, pp. 5639–5640 David A. Leigh.

(List continued on next page.)

Primary Examiner—Ellen M McAvoy (57) ABSTRACT

Low molecular weight oxazine ring-containing Mannich base condensates of hydroxy aromatic compounds, aldehyde; and amine. Such compounds are useful as soot dispersants in lubricating oils when used alone, or in combination with high molecular weight dispersants.

15 Claims, 2 Drawing Sheets

U.S. PATENT DOCUMENTS

| | | | |
|---|---|---|---|
| 3,632,511 A | 1/1972 | Liao | 252/51.5 A |
| 3,634,515 A | 1/1972 | Piasek et al. | 260/570.5 |
| 3,649,229 A | 3/1972 | Otto | 44/73 |
| 3,726,882 A | 4/1973 | Traise et al. | 260/296 |
| 3,798,165 A | 3/1974 | Piasek et al. | 252/51.5 R |
| 3,798,247 A | 3/1974 | Piasek et al. | 260/404.5 |
| 3,912,764 A | 10/1975 | Palmer | 260/346.8 |
| 3,980,569 A | 9/1976 | Pindar et al. | 252/51.5 R |
| 4,102,798 A | 7/1978 | Ryer et al. | 252/51.5 A |
| 4,110,349 A | 8/1978 | Cohen | 260/346.74 |
| 4,113,639 A | 9/1978 | Lonstrup et al. | 252/51.5 A |
| 4,116,876 A | 9/1978 | Brois et al. | 252/49.6 |
| 4,234,435 A | 11/1980 | Meinhardt et al. | 252/51.5 A |
| 4,313,738 A * | 2/1982 | Parlman et al. | 44/334 |
| 4,354,950 A | 10/1982 | Hammond et al. | 252/51.5 A |
| 4,396,517 A | 8/1983 | Gemmill et al. | 252/51.5 A |
| 4,857,217 A | 8/1989 | Gutierrez et al. | 252/47 |
| 4,867,890 A | 9/1989 | Colclough et al. | 252/327 E |
| 4,952,739 A | 8/1990 | Chen | 585/18 |
| 4,956,107 A | 9/1990 | Gutierrez et al. | 252/47 |
| 4,963,275 A | 10/1990 | Gutierrez et al. | 252/47 |
| 5,017,299 A | 5/1991 | Gutierrez et al. | 252/51.5 R |
| 5,053,152 A | 10/1991 | Steckel | 252/51.5 R |
| 5,186,851 A | 2/1993 | Gutierrez et al. | 252/49.006 |
| 5,229,022 A | 7/1993 | Song et al. | 252/56 R |
| 5,334,775 A | 8/1994 | Gutierrez et al. | 568/791 |
| 5,345,002 A | 9/1994 | Song et al. | 568/793 |
| 5,498,809 A | 3/1996 | Emert et al. | 585/13 |
| 5,580,484 A | 12/1996 | Gutierrez | 508/238 |
| 5,663,130 A | 9/1997 | Emert et al. | 508/506 |
| 5,705,577 A | 1/1998 | Rossi et al. | 526/68 |
| 5,814,715 A | 9/1998 | Chen et al. | 526/348.6 |
| 6,022,929 A | 2/2000 | Chen et al. | 525/333.7 |
| 6,030,930 A | 2/2000 | Emert et al. | 508/312 |
| 6,495,496 B2 * | 12/2002 | Gutierrez et al. | 508/561 |

OTHER PUBLICATIONS

Shen, Ai Yu et al., "Synthesis and testing of naphthol derivatives as antimicrobial agents" ACTA Pharmaceutica (1994), 44(2), pp. 117–126, XP001106956.

Valk, Jean–Marc et al., "Carbon–hydrogen and C–X (X=Cl or SiMe3) bond activation. 1–Cyclopalladation and oxidation of some derivatives of 2-'(dimethylamino)methylnaphthalene", Journal of the Chemical Society, Dalton Translations: Inorganic Chemistry (1972–1999) (1994), (15), 2292–302, XP001106266.

Moehrle, Hans et al., "Model reactions for plumbagin synthesis, Part 1. Monoaminoalkylation of 1,5–naphthalenediol with subsequent hydrogenolysis", Z. Naturforsch, B: Chem. Sci. (1987), 42(9), 1181–6, No. 42b, 1987, pp. 1181–1186, XP001106907.

Kimura, Masaru et al.: "The reaction of diaralkylglycines: preparation and chemistry of N–chloromethyldibenzylamine hydrochloride", Chem. Lett. (1977), (9), 1035–8, 1977, pp. 1035–1038, XP001106281.

Cameron, D.W.: "Side–chain versus Nuclear Amination of Methyl–substituted Benzo– and Naphto–quinones", Journal of Chemical Society, No. 9, pp. 1245–1251, XP001117510.

* cited by examiner

HYDROXY AROMATIC MANNICH BASE CONDENSATION PRODUCTS AND THE USE THEREOF AS SOOT DISPERSANTS IN LUBRICATING OIL COMPOSITIONS

This application is a continuation-in-part of U.S. patent application Ser. No. 09/746,038 filed Dec. 22, 2000 now U.S. Pat. No. 6,495,496 and U.S. patent application Ser. No. 10/209,522 filed Jul. 30, 2002.

FIELD OF THE INVENTION

This invention relates to a novel class of Mannich base condensation products that act as potent soot dispersants in lubricating oil compositions. The invention is further directed to lubricating oil compositions containing said soot dispersants.

BACKGROUND OF THE INVENTION

Lubricating oil compositions comprise a major amount of base oil and additives that improve the performance and increase the useful life of the lubricant. Nitrogen-containing dispersants are commonly used lubricant additives. The function of a dispersant is to maintain in suspension within the oil, insoluble materials formed by oxidation and other mechanisms during use of the oil, to prevent sludge flocculation and precipitation of the insoluble materials. Another function of the dispersant is to reduce the agglomeration of soot particles, thus reducing increases in the viscosity of the lubricating oil upon use. Crankcase lubricants providing improved performance, including improved soot dispersancy, have been continuously demanded.

To improve the sludge dispersing characteristic of lubricating oils, industry has moved to the use higher molecular weight materials, which have superior sludge dispersing properties compared to lower molecular weight materials, and have used such high molecular weight dispersants in ever increasing amounts. However, dispersants are expensive, may contain residual levels of chlorine, which leads to problems with the disposal of used lubricants, do not blend well in lubricants also containing overbased detergents and contain a high level of basic amine, which causes the deterioration of seals within the engine during service. In addition, high molecular weight dispersants, even when used in greater amounts, do not provide sufficient soot dispersing properties, particularly in high soot environments as are encountered with lubricating oils for heavy duty diesel engines. Therefore, it would be advantageous to be able to provide a lubricant with adequate soot dispersancy properties, and preferably, to do so using reduced amounts of high molecular weight dispersant.

U.S. Pat. No. 3,442,808 relates to lubricating oil additives prepared by reacting alkenyl succinic anhydride with a Mannich base condensation product prepared by condensing alkyl substituted phenol, formaldehyde and polyalkylene polyamine.

U.S. Pat. No. 3,458,495 relates to oxidation inhibitors and dispersant-detergent oil additives comprising the reaction product of one equivalent of a phosphosulfurized hydrocarbon and about 0.5 to 4 equivalents of an alkylene amino phenol. The phosphosulfurized hydrocarbons are prepared by reacting a terpene, a petroleum fraction or a 500 to 200,000 molecular weight $C_2$ to $C_6$ olefin polymer (including polymers of ethylene, propylene, butylene, isobutylene or isoamylene) and from 5 to 40 wt % of a sulfide of phosphorous. The alkylene amino phenol is prepared by a Mannich base condensation of aldehyde, alkylene polyamine and alkyl phenol.

U.S. Pat. No. 4,354,950 discloses a method of preparing Mannich base derivatives of hydroxyaryl succinimides of the formula:

wherein R is hydrocarbyl of 25 to 200 carbon atoms, R' is H, alkyl or halogen, "n" is 2 or 3, "m" has a value of 1 to 5, Y is H or a methylene hydroxyaryl succinimide radical, "x" has a value of 1 to 2 when Y is H and a value of 1 when Y is a methylene hydroxyaryl succinimide radical. The above succinimides are formed in a stepwise reaction, e.g., by reacting a polyalkenyl succinic anhydride with an aminophenol to produce an intermediate N-(hydroxyaryl) hydrocarbyl succinimide, which is then reacted with an alkylene diamine and an aldehyde (e.g., formaldehyde) in a Mannich base reaction to produce the desired product. The resulting succinimides may be added to base oil of lubricating viscosity to form lubricant concentrates and lubricating oil formulations.

U.S. Pat. Nos. 5,017,299; 5,186,851 and 5,345,002 describe Mannich base condensates of alkyl substituted hydroxy aromatic compounds with formaldehyde and an amine, wherein the alkyl-moiety of the aromatic compound is derived from ethylene alpha-olefin copolymer having a number average molecular weight of 300 to 10,000, and wherein at least 30% of the polymer's chains contain a terminal ethenylidene unsaturation.

U.S. Pat. No. 5,580,484 describes a succinimide Mannich base condensate of an alkyl substituted hydroxy aromatic compound, an aldehyde and a "heavy polyamine" defined as a mixture of polyalkylenepolyamines comprising small amounts of lower polyamine oligomers, such as tetraethylene pentamine and pentahexamine, and a large majority of oligomers with 7 or more nitrogens and 2 or more primary amines per molecule, and a greater degree of branching compared to conventional polyamine mixtures. Again, the alkyl-moiety of the aromatic compound is described as being derived from a polymer backbone having a number average molecular weight of greater than 300.

SUMMARY OF THE INVENTION

In accordance with one aspect of the present invention, there are provided novel Mannich base condensates of hydroxy aromatic compounds, optionally substituted with one or more hydrocarbyl moieties; an aldehyde; and an amine.

In accordance with another aspect of the present invention, a lubricating oil composition is provided which comprises a base oil of lubricating viscosity and an effective amount of a soot dispersant which are Mannich base condensates of hydroxy aromatic compounds, optionally substituted with one or more hydrocarbyl moieties; an aldehyde; and an amine.

In accordance with still another aspect of the present invention, there is provided a lubricating oil composition or concentrate which comprises a base oil of lubricating viscosity and an effective amount of (1) certain Mannich base condensate of a hydroxy aromatic compound, optionally substituted with one or more hydrocarbyl moieties; an aldehyde; and a primary or secondary amine, and (2) a high molecular weight nitrogen-containing dispersant.

Compared to the Mannich base materials of the prior art, the lower molecular weight materials of the invention provide lubricating oils with superior soot dispersing characteristics and, when used in combination with conventional high molecular weight nitrogen-containing dispersant, synergistically enhance the inherent soot dispersing properties of the high molecular weight dispersant. As an added benefit, the addition of the Mannich base materials of the present invention to a lubricating oil composition provides an antioxidancy credit.

DETAILED DESCRIPTION OF THE INVENTION

The compounds of the present invention are the condensation products of mono- or polynuclear aromatic compounds optionally substituted with hydrocarbyl; a $C_1$–$C_{10}$ aldehyde; and an amine containing from 1 to 60 carbon atoms and from 1 to about 12 nitrogens per molecule. Such compounds can be represented by formula (I):

(I)

wherein:

Ar is a mono- or polynuclear aromatic moiety;

$R_1$ and $R_2$ are independently selected from H and $C_1$–$C_{30}$ straight or branched chain hydrocarbyl groups optionally containing one or more hetero atoms selected from N, O and S;

$R_3$ is a straight or branched chain hydrocarbyl group;

$R_4$ is H or a $C_1$ to $C_9$ straight or branched chain hydrocarbyl group;

q is 1 or 2;

x is 1 to 3;

y is from 1 to 2 times the number of aromatic rings in Ar; and z is zero to a number equal to the number of remaining substitutable hydrogens on aromatic moiety Ar;

with the proviso that a hydroxyl group attached to Ar can combine with N—$R_1$ to form a substituted or unsubstituted 6 membered oxazine ring, provided that, when a hydroxyl group attached to Ar combines with N—$R_1$ to form a substituted or unsubstituted 6 membered oxazine ring, and z is 0, $R_2$ is not H.

Hydroxy aromatic compounds useful in the preparation of the materials of this invention include those compounds of formula (II):

wherein Ar represents a mono- or polynuclear aromatic moiety and y is from 1 to 2 times the number of aromatic rings in Ar. Polynuclear moieties may comprise two or more fused rings, each ring having 4 to 10 carbon atoms (e.g., naphthalene). Suitable polynuclear moieties may also be linked mononuclear aromatic moieties, such as biphenyl, or may comprise linked, fused rings (e.g., binaphthyl). Examples of suitable polynuclear aromatic moieties include phenylene, bi-phenyl, tetralin, naphthalene, binaphthyl, anthracene, phenanthrene, fluorene, indene, cyclopentenophenanthrene, benzanthracene, dibenzanthracene, chrysene, pyrene, benzpyrene and coronene. Preferred aromatic moieties include phenylene and naphthalene with naphthalene being particularly preferred.

The hydroxy aromatic compounds useful in the present invention are optionally substituted with one or more hydrocarbyl moieties. To alkylate the hydroxy aromatic compound, the selected hydrocarbyl moiety (a straight or branched chain hydrocarbyl group) and hydroxy aromatic compound can be contacted in the presence of a catalytically effective amount of at least one acidic alkylation catalyst under conditions effective to alkylate the aromatic group of the hydroxy aromatic compound. The alkylation catalyst is conventional and can comprise inorganic acids such as $H_3PO_4$, $H_2SO_4$, HF, $BF_3$, HF—$BF_3$ and the like. The acid catalyst can also comprise an acidic ion exchange resin having acidic groups adsorbed or absorbed thereon, such as Amberlyst 15 resin (Rohm & Haas Co.), and the like. Also useful as catalysts are preformed complexes (or complexes formed in situ) of the foregoing with $C_2$ to $C_{10}$ ethers, $C_1$ to $C_{10}$ alcohols, $C_2$ to $C_{10}$ ketones, phenols and the like, such as $BF_3$ complexed with dimethyl ether, diethyl ether, phenol, and the like. Other useful alkylation catalysts include clay catalysts, such as Filterols F20X, F22, F105SF and the like (Englehard Chemical Corp.), and heteropoly acids catalysts, as described for example, in U.S. Pat. No. 5,334,775.

The hydroxy aromatic compound and hydrocarbyl moiety will generally be contacted in a ratio of from about 0.1 to 10, preferably from about 1 to 7, more preferably from about 2 to 5, moles of the aromatic compound per mole of hydrocarbyl moiety. The selected acid catalyst can be employed in widely varying concentrations. Generally, when the acid catalyst comprises an inorganic catalyst, the acid catalyst will be charged to provide at least about 0.001, preferably from about 0.01 to 0.5, more preferably from about 0.1 to 0.3 moles of catalyst per mole of hydroxy aromatic compound charged to the alkylation reaction zone. The use of greater than 1 mole of the inorganic catalyst per mole of hydroxy aromatic compound is not generally required. When the acid catalyst comprises a supported catalyst, such as an acidic ion exchange resin, the reactants can be contacted with the ion exchange resin employing any conventional solid-liquid contacting techniques, such as by passing the reactants through the resin (e.g., in a catalyst bed or through a membrane impregnated or otherwise containing the resin catalyst) and the upper limit on the moles of catalyst employed per mole of hydroxy aromatic compound is not critical.

The temperature for alkylation can also vary widely, and will usually range from about 20 to about 250° C., preferably from about 30 to about 150° C., more preferably from about 50 to about 80° C.

The alkylation reaction time can vary and will generally be from about 1 to 5 hours, although longer or shorter times can also be employed. The alkylation process can be practiced in a batchwise, continuous or semi-continuous manner. Preferably, the acid catalyst is neutralized and/or removed prior to contacting the alkylation product mixture with the amine reagent (e.g., polyamine) and aldehyde reactant. The neutralization can be accomplished by contacting the crude alkylation product with gaseous ammonia or other basically reacting compound (e.g., aqueous NaOH, KOH and the like), followed by filtration to remove any precipitated neutralized catalyst solids. The hydrocarbyl moiety may be a single linear or branched chain hydrocarbyl group, or may comprise a mixture of such hydrocarbyl groups. Alkylation processes of the above types are known and are described for example, in U.S. Pat. Nos. 3,539,633 and 3,649,229.

Alkylated hydroxy aromatic compounds useful in the practice of the present invention may alternatively be provided by first alkylating an aromatic compound (e.g. naphthalene), using, for example, the alkylation methods described above, and subsequently oxidating the alkylated aromatic compound. Methods for forming such compounds are well known and described for example, in U.S. Pat. Nos. 2,407,044; 2,407,055; 2,451,996 and 3,033,903.

The aldehyde reactant useful in the formation of the Mannich Base condensation products of the present invention will generally comprise formaldehyde or paraformaldehyde, although it will be understood that other aldehyde-group containing compounds, such as $C_2$ to $C_{10}$ hydrocarbyl aldehydes (e.g., butyraldehyde, acetaldehyde, propionaldehyde, and the like) can also be employed. A preferred group of aldehyde materials are compounds of the formula R"CHO, wherein R" is H or aliphatic hydrocarbon radical having from 1 to 4 carbon atoms.

Amine compounds useful for reaction with the selected hydroxyaromatic compound and aldehyde materials are primary or secondary amines, aliphatic or aromatic amines, or amine salts. Suitable amines include mono- and polyamines, of about 2 to 60, preferably 2 to 40 (e.g. 3 to 20), total carbon atoms and about 1 to 12, preferably 1 to 5, and most preferably 1 to 3 nitrogen atoms in the molecule. When more than 12 nitrogen atoms are present in the molecule, gelation of the reaction mixture may occur. These amines may be hydrocarbyl amines or may be hydrocarbyl amines including other groups, e.g., hydroxy groups, alkoxy groups, amide groups, nitriles, imidazoline groups, and the like. Hydroxy amines with 1 to 6 hydroxy groups, preferably 1 to 3 hydroxy groups are particularly useful. Preferred amines are aliphatic saturated amines, including those of the general formulas:

(III)

(IV)

wherein R, R', R" and R'" are independently selected from the group consisting of hydrogen; $C_1$ to $C_{25}$ straight or branched chain alkyl radicals; $C_1$ to $C_{12}$ alkoxy, $C_2$ to $C_6$ alkylene radicals; $C_2$ to $C_{12}$ hydroxy amino alkylene radicals; and $C_1$ to $C_{12}$ alkylamino $C_2$ to $C_6$ alkylene radicals; and wherein R'" can additionally comprise a moiety of the formula:

(V)

wherein R' is as defined above, and wherein r and r' can be the same or a different number of from about 2 to about 6, preferably about 2 to about 4; and t and t' can be the same or different and are numbers of from 0 to about 10, preferably 0 to about 3, and most preferably about 0 to about 2, with the proviso that the sum of t and t' is not greater than about 10. To assure a facile reaction, it is preferred that R, R', R", R'", r, r', t and t' be selected in a manner sufficient to provide the compounds of Formulas III and IV with typically at least one primary or secondary amine group, preferably at least two primary or secondary amine groups. This can be achieved by selecting at least one of said R, R', R" or R'" groups to be hydrogen or by letting t in Formula IV be at least one when R'" is H or when the moiety of moiety V possesses a secondary amino group. The most preferred amines of the above formulas are represented by Formula III.

Non-limiting examples of suitable amine compounds include: 1,2-diaminoethane; 1,3-diaminopropane; 1,4-diaminobutane; 1,6-diaminohexane; polyethylene amines such as diethylene triamine; triethylene tetramine; tetraethylene pentamine; polypropylene amines such as 1,2-propylene diamine; di-(1,2-propylene)triamine; di-(1,3-propylene) triamine; N,N-dimethyl-1,3-diaminopropane; N,N-di-(2-aminoethyl) ethylene diamine; N,N-di(2-hydroxyethyl)-1,3-propylene diamine; 3-dodecyloxypropylamine; N-dodecyl-1,3-propane diamine; diisopropanol amine; diethanol amine; mono- and di-tallow amines, mono- and di-coco amines, mono- and di-palmitic amines; di-phenyl amine, di-benzyl amine; morpholines such as N-(3-aminopropyl)morpholine; and mixtures thereof.

Other useful amine compounds include: alicyclic diamines such as 1,4-di(aminomethyl) cyclohexane, and heterocyclic nitrogen compounds such as imidazolines, and N-aminoalkyl piperazines of the general formula (VI):

(VI)

wherein $p_1$ and $P_2$ are the same or different and are each integers of from about 1 to about 4, and $n_1$, $n_2$ and $n_3$ are the same or different and are each integers of from 0 to about 3 with the proviso that the amine has no more than about 12 nitrogen atoms per molecule. Non-limiting examples of such amines include 2-pentadecyl imidazoline; N-(2-aminoethyl) piperazine; etc.

Commercial mixtures of amine compounds may advantageously be used. For example, one process for preparing alkylene amines involves the reaction of an alkylene dihalide (such as ethylene dichloride or propylene dichloride) with ammonia, which results in a complex mixture of alkylene amines wherein pairs of nitrogens are joined by alkylene groups, forming such compounds as diethylene triamine, triethylenetetramine, tetraethylene pentamine and isomeric piperazines. Low cost poly(ethyleneamines) compounds averaging about 5 to 7 nitrogen atoms per molecule are available commercially under trade names such as "Polyamine H", "Polyamine 400", "Dow Polyamine E-100", etc. "Heavy polyamine" mixtures, as defined in U.S. Pat. No. 5,580,484 described supra, may also be employed.

Useful amines also include polyoxyalkylene polyamines such as those of the formula (VII) and (VIII):

(VII)

(VIII)

where R'''' is H or $C_1$–$C_{22}$ alkyl, preferably $C_1$–$C_5$ alkyl, and n4 is 1 to 3.

The Mannich base condensation products of this invention are prepared by condensing at least one of the above-described hydroxy aromatic compounds with an amine in the presence of an aldehyde. The reactants are contacted for a time and under conditions sufficient to form the desired dispersant product. The process employed in the condensation reaction can be any of those disclosed in U.S. Pat. Nos. 3,634,515; 3,649,229; 3,442,808; 3,798,165; 3,798,247 and 3,539,633.

The amount of the reactants employed is not critical and can vary over a wide range. It is, however, preferred to react the hydroxy aromatic compound, aldehyde reactant and amine compound in the respective molar ratios of about 1:1–4:0.1–10. An excess of aldehyde reactant may be used. An excess of aldehyde reactant over amine reaction favor formation of compounds containing an oxazine ring. When compounds containing an oxazine ring are desired, the hydroxy aromatic compound, aldehyde reactant and amine compound are preferably reacted in respective molar ratios of about 1:1–2:1, when x is 1, and 1:2–3:2, when x is 2. The reactions are exothermic, but it is desirable to heat the reaction to a temperature of above about 150° C., preferably in the range of form about 150–200° C. This additional heating drives the reaction to completion and removes water from the resulting condensation reaction product.

The Mannich base condensation reaction is represented by the following reaction schemes:

+ wherein $R_1$ and $R_2$ are as previously defined.

A preferred group of Mannich base condensation products are those formed by condensing napthol, optionally substituted with hydrocarbyl, with formaldehyde and an aliphatic or aromatic substituted secondary amine, e.g., fatty amines such as hydrogenated mono- or di-tallow amine, mono- or di-coco amine; amines substituted with shorter alkyl moieties, such as mono- or di-nonyl amine, mono- or di-octyl amine, mono- or di-hexyl amine, mono- or di-pentyl amine, mono- or di-butyl amine, mono- or di-propyl amine, mono- or di-methyl amine; or mono- or di-phenyl or mono- or di-benzyl amine. Particularly preferred are di-alkyl amines derived from natural fatty acids, such as di-coco amine, di-tallow amine and di-palmitic amine. A particularly preferred product of the present invention comprises the condensation reaction of (A) naphthol; (B) formaldehyde; and (C) a di-alkyl amine derived from a natural fatty acid; using about 1 to 2 moles of each of (B) and (C) per mole of (A). Preferably, the naphthol is substituted with hydrocarbyl. The hydrocarbyl can comprise a low molecular alkyl moiety, such as methyl or ethyl, or can be oligomeric or polymeric (e.g., polyisobutene (PIB)). The desired Mannich Base condensation product formed by the process of this invention will generally be present in the condensation reaction product mixture in a concentration of at least about 60 wt. % (e.g., from 65 to 95 wt. %), more preferably at least about 70 wt. %, and most preferably from about 75 to about 90 wt. %.

The Mannich base condensation products of the present invention provide soot dispersing properties to lubricating oils when blended therewith. Oils of lubricating viscosity useful in the context of the present invention may be selected from natural lubricating oils, synthetic lubricating oils and mixtures thereof. The lubricating oil may range in viscosity from light distillate mineral oils to heavy lubricating oils such as gasoline engine oils, mineral lubricating oils and heavy duty diesel oils. Generally, the viscosity of the oil ranges from about 2 centistokes to about 40 centistokes, especially from about 4 centistokes to about 20 centistokes, as measured at 100° C.

Natural oils include animal oils and vegetable oils (e.g., castor oil, lard oil); liquid petroleum oils and hydrorefined, solvent-treated or acid-treated mineral oils of the paraffinic, naphthenic and mixed paraffinic-naphthenic types. Oils of lubricating viscosity derived from coal or shale also serve as useful base oils.

Synthetic lubricating oils include hydrocarbon oils and halo-substituted hydrocarbon oils such as polymerized and interpolymerized olefins (e.g., polybutylenes, polypropylenes, propylene-isobutylene copolymers, chlorinated polybutylenes, poly(1-hexenes), poly(1-octenes), poly (1-decenes)); alkylbenzenes (e.g., dodecylbenzenes, tetradecylbenzenes, dinonylbenzenes, di(2-ethylhexyl) benzenes); polyphenyls (e.g., biphenyls, terphenyls, alkylated polyphenols); and alkylated diphenyl ethers and alkylated diphenyl sulfides and derivative, analogs and homologs thereof.

Alkylene oxide polymers and interpolymers and derivatives thereof where the terminal hydroxyl groups have been modified by esterification, etherification, etc., constitute another class of known synthetic lubricating oils. These are exemplified by polyoxyalkylene polymers prepared by polymerization of ethylene oxide or propylene oxide, and the alkyl and aryl ethers of polyoxyalkylene polymers (e.g., methyl-polyiso-propylene glycol ether having a molecular weight of 1000 or diphenyl ether of poly-ethylene glycol having a molecular weight of 1000 to 1500); and mono- and polycarboxylic esters thereof, for example, the acetic acid esters, mixed $C_3$–$C_8$ fatty acid esters and $C_{13}$ Oxo acid diester of tetraethylene glycol.

Another suitable class of synthetic lubricating oils comprises the esters of dicarboxylic acids (e.g., phthalic acid, succinic acid, alkyl succinic acids and alkenyl succinic acids, maleic acid, azelaic acid, suberic acid, sebasic acid, fumaric acid, adipic acid, linoleic acid dimer, malonic acid, alkylmalonic acids, alkenyl malonic acids) with a variety of alcohols (e.g., butyl alcohol, hexyl alcohol, dodecyl alcohol, 2-ethylhexyl alcohol, ethylene glycol, diethylene glycol monoether, propylene glycol). Specific examples of such esters includes dibutyl adipate, di(2-ethylhexyl) sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, and the complex ester formed by reacting one mole of sebacic acid with two moles of tetraethylene glycol and two moles of 2-ethylhexanoic acid.

Esters useful as synthetic oils also include those made from $C_5$ to $C_{12}$ monocarboxylic acids and polyols and polyol esters such as neopentyl glycol, trimethylolpropane, pentaerythritol, dipentaerythritol and tripentaerythritol.

Silicon-based oils such as the polyalkyl-, polyaryl-, polyalkoxy- or polyaryloxysilicone oils and silicate oils comprise another useful class of synthetic lubricants; such oils include tetraethyl silicate, tetraisopropyl silicate, tetra-(2-ethylhexyl)silicate, tetra-(4-methyl-2-ethylhexyl)silicate, tetra-(p-tert-butyl-phenyl) silicate, hexa-(4-methyl-2-ethylhexyl)disiloxane, poly(methyl)siloxanes and poly (methylphenyl)siloxanes. Other synthetic lubricating oils include liquid esters of phosphorous-containing acids (e.g., tricresyl phosphate, trioctyl phosphate, diethyl ester of decylphosphonic acid) and polymeric tetrahydrofurans.

Unrefined, refined and re-refined oils can be used in lubricants of the present invention. Unrefined oils are those obtained directly from a natural or synthetic source without further purification treatment. For example, a shale oil obtained directly from retorting operations; petroleum oil obtained directly from distillation; or ester oil obtained directly from an esterification and used without further treatment would be unrefined oil. Refined oils are similar to unrefined oils except that the oil is further treated in one or more purification steps to improve one or more properties. Many such purification techniques, such as distillation, solvent extraction, acid or base extraction, filtration and percolation are known to those skilled in the art. Re-refined oils are obtained by processes similar to those used to provide refined oils but begin with oil that has already been used in service. Such re-refined oils are also known as reclaimed or reprocessed oils and are often subjected to additionally processing using techniques for removing spent additives and oil breakdown products.

The Mannich base condensation products of the present invention can be incorporated into lubricating oil in any convenient way. Thus, the compounds of the invention can be added directly to the oil by dispersing or dissolving the same in the oil at the desired level of concentrations. Such blending into the lube oil can occur at room temperature or elevated temperatures. Alternatively, the compounds of the invention can be blended with a suitable oil-soluble solvent and base oil to form a concentrate, which concentrate can then be blended with a lubricating oil basestock to obtain the final formulation. Such concentrates will typically contain (on an active ingredient (A.I.)) basis from about 20 to about 60 wt. %, and preferably from about 40 to about 50 wt. %, of the inventive compound, and typically from about 40 to 80 wt. %, preferably from about 40 to 60 wt. %, base oil, based on the concentrate weight. To provide sufficient soot dispersing characteristics, the fully formulated lubricating oil composition should contain from about 0.01 to about 10 wt. %, preferably from about 0.1 to about 5 wt. %, most preferably from about 0.1 to about 1 wt. % of one or more compounds of the present invention.

Because the Mannich base condensation products of the present invention do not alone provide a lubricating oil composition with sufficient sludge dispersing properties, lubricating oil compositions containing the Mannich base condensation products of the present invention may also contain a conventional high molecular weight dispersant.

The high molecular weight dispersants useful in the context of the present invention include the range of ashless (metal-free) dispersants known to be effective to reduce formation of deposits upon use in gasoline and diesel engines, when added to lubricating oils. The ashless, high molecular weight dispersant useful in the compositions of the present invention comprises an oil soluble polymeric long chain backbone having functional groups capable of associating with particles to be dispersed. Typically, such dispersants comprise amine, alcohol, amide or ester polar moieties attached to the polymer backbone, often via a bridging group. The ashless, high molecular weight dispersant may be, for example, selected from oil soluble salts, esters, amino-esters, amides, imides and oxazolines of long chain hydrocarbon-substituted mono- and polycarboxylic acids or anhydrides thereof; thiocarboxylate derivatives of long chain hydrocarbons; long chain aliphatic hydrocarbons having polyamine moieties attached directly thereto; and Mannich condensation products formed by condensing a long chain substituted phenol with formaldehyde and polyalkylene polyamine.

A "high molecular weight" dispersant is one having a number average molecular weight greater than or equal to 450, such as between 450 and 20,000. The precise molecular weight ranges will depend on the type of polymer used to form the dispersant, the number of functional groups, and the type of polar functional group employed. For example, for a polyisobutylene derivatized dispersant, a high molecular weight dispersant may be one formed with a polymer backbone having a number average molecular weight of from about 1700 to about 5600. Typical commercially available polyisobutylene-based dispersants contain polyisobutylene polymers having a number average molecular weight ranging from about 900 to about 2300, functionalized by maleic anhydride (MW=98), and derivatized with polyamines having a molecular weight of from about 100 to about 350. Polymers of low molecular weight could also be used to form a high molecular weight dispersant by incorporating multiple polymer chains into the dispersant using methods known in the art.

Polymer molecular weight, specifically $\overline{M}_n$, can be determined by various known techniques. One convenient method is gel permeation chromatography (GPC), which additionally provides molecular weight distribution information (see W. W. Yau, J. J. Kirkland and D. D. Bly, "Modern Size Exclusion Liquid Chromatography", John Wiley and Sons, New York, 1979). If the molecular weight of an amine-containing dispersant (e.g., PIBSA-polyamine) is being determined, the presence of the amine may cause the dispersant to be adsorbed by the column, leading to an inaccurate molecular weight determination. Persons familiar with the operation of GPC equipment understand that this problem may be eliminated by using a mixed solvent system, such as tetrahydrofuran (THF) mixed with a minor amount of pyridine, as opposed to pure THF. The problem may also be addressed by capping the amine with acetic anhydride and correcting the molecular weight based on the amount of capping groups. Another useful method for determining molecular weight, particularly for lower molecular weight polymers, is vapor pressure osmometry (see, e.g., ASTM D3592).

Suitable hydrocarbons or polymers employed in the formation of conventional high molecular weight dispersants include homopolymers, interpolymers or lower molecular weight hydrocarbons. One family of such polymers comprise polymers of ethylene and/or at least one $C_3$ to $C_{28}$ alpha-olefin having the formula $H_2C=CHR^1$ wherein $R^1$ is straight or branched chain alkyl radical comprising 1 to 26 carbon atoms and wherein the polymer contains carbon-to-carbon unsaturation, preferably a high degree of terminal ethenylidene unsaturation. Preferably, such polymers comprise interpolymers of ethylene and at least one alpha-olefin of the above formula, wherein $R^1$ is alkyl of from 1 to 18 carbon atoms, and more preferably is alkyl of from 1 to 8 carbon atoms, and more preferably still of from 1 to 2 carbon atoms. Therefore, useful alpha-olefin monomers and comonomers include, for example, propylene, butene-1, hexene-1, octene-1,4-methylpentene-1, decene-1, dodecene-1, tridecene-1, tetradecene-1, pentadecene-1, hexadecene-1, heptadecene-1, octadecene-1, nonadecene-1, and mixtures thereof (e.g., mixtures of propylene and butene-1, and the like). Exemplary of such polymers are propylene homopolymers, butene-1 homopolymers, ethylene-propylene copolymers, ethylene-butene-1 copolymers, propylene-butene copolymers and the like, wherein the polymer contains at least some terminal and/or internal unsaturation. Preferred polymers are unsaturated copolymers of ethylene and propylene and ethylene and butene-1. The interpolymers of this invention may contain a minor amount, e.g. 0.5 to 5 mole % of a $C_4$ to $C_{18}$ non-conjugated diolefin comonomer. However, it is preferred that the polymers of this invention comprise only alpha-olefin homopolymers, interpolymers of alpha-olefin comonomers and interpolymers of ethylene and alpha-olefin comonomers. The molar ethylene content of the polymers employed in this invention is preferably in the range of 20 to 80%, and more preferably 30 to 70%. When propylene and/or butene-1 are employed as comonomer(s) with ethylene, the ethylene content of such copolymers is most preferably between 45 and 65%, although higher or lower ethylene contents may be present.

These polymers may be prepared by polymerizing alpha-olefin monomer, or mixtures of alpha-olefin monomers, or mixtures comprising ethylene and at least one $C_3$ to $C_{28}$ alpha-olefin monomer, in the presence of a catalyst system comprising at least one metallocene (e.g., a cyclopentadienyl-transition metal compound) and an alumoxane compound. Using this process, a polymer in which 95% or more of the polymer chains possess terminal ethenylidene-type unsaturation can be provided. The percentage of polymer chains exhibiting terminal ethenylidene unsaturation may be determined by FTIR spectroscopic analysis, titration, or $C^{13}$ NMR. Interpolymers of this latter type may be characterized by the formula POLY-C($R^1$)=$CH_2$ wherein $R^1$ is $C_1$ to $C_{26}$ alkyl, preferably $C_1$ to $C_{18}$ alkyl, more preferably $C_1$ to $C_8$ alkyl, and most preferably $C_1$ to $C_2$ alkyl, (e.g., methyl or ethyl) and wherein POLY represents the polymer chain. The chain length of the $R^1$ alkyl group will vary depending on the comonomer(s) selected for use in the polymerization. A minor amount of the polymer chains can contain terminal ethenyl, i.e., vinyl, unsaturation, i.e. POLY-CH=$CH_2$, and a portion of the polymers can contain internal monounsaturation, e.g. POLY-CH=CH($R^1$), wherein $R^1$ is as defined above. These terminally unsaturated interpolymers may be prepared by known metallocene chemistry and may also be prepared as described in U.S. Pat. Nos. 5,498,809; 5,663,130; 5,705,577; 5,814,715; 6,022,929 and 6,030,930.

Another useful class of polymers is polymers prepared by cationic polymerization of isobutene, styrene, and the like. Common polymers from this class include polyisobutenes obtained by polymerization of a $C_4$ refinery stream having a butene content of about 35 to about 75% by wt., and an isobutene content of about 30 to about 60% by wt., in the presence of a Lewis acid catalyst, such as aluminum trichloride or boron trifluoride. A preferred source of monomer for making poly-n-butenes is petroleum feedstreams such as Raffinate II. These feedstocks are disclosed in the art such as in U.S. Pat. No. 4,952,739. Polyisobutylene is a most preferred backbone of the present invention because it is readily available by cationic polymerization from butene streams (e.g., using $AlCl_3$ or $BF_3$ catalysts). Such polyisobutylenes generally contain residual unsaturation in amounts of about one ethylenic double bond per polymer chain, positioned along the chain.

As noted above, the polyisobutylene polymers employed are generally based on a hydrocarbon chain of from about 900 to 2,300. Methods for making polyisobutylene are known. Polyisobutylene can be functionalized by halogenation (e.g. chlorination), the thermal "ene" reaction, or by free radical grafting using a catalyst (e.g. peroxide), as described below.

Processes for reacting polymeric hydrocarbons with unsaturated carboxylic acids, anhydrides or esters and the preparation of derivatives from such compounds are disclosed in U.S. Pat. Nos. 3,087,936; 3,172,892; 3,215,707; 3,231,587; 3,272,746; 3,275,554; 3,381,022; 3,442,808; 3,565,804; 3,912,764; 4,110,349; 4,234,435; and GB-A-1, 440,219. The polymer or hydrocarbon may be functionalized, for example, with carboxylic acid producing moieties (preferably acid or anhydride) by reacting the polymer or hydrocarbon under conditions that result in the addition of functional moieties or agents, i.e., acid, anhydride, ester moieties, etc., onto the polymer or hydrocarbon chains primarily at sites of carbon-to-carbon unsaturation (also referred to as ethylenic or olefinic unsaturation) using the halogen assisted functionalization (e.g. chlorination) process or the thermal "ene" reaction.

When using the free radical grafting process using a catalyst (e.g. peroxide), the functionalization is randomly effected along the polymer chain. Selective functionalization can be accomplished by halogenating, e.g., chlorinating or brominating the unsaturated α-olefin polymer to about 1 to 8 wt. %, preferably 3 to 7 wt. % chlorine, or bromine, based on the weight of polymer or hydrocarbon, by passing the chlorine or bromine through the polymer at a temperature of 60 to 250° C., preferably 110 to 160° C., e.g., 120 to 140° C., for about 0.5 to 10, preferably 1 to 7 hours. The halogenated polymer or hydrocarbon (hereinafter backbone) is then reacted with sufficient monounsaturated reactant capable of adding functional moieties to the backbone, e.g., monounsaturated carboxylic reactant, at 100 to 250° C., usually about 180° C. to 235° C., for about 0.5 to 10, e.g., 3 to 8 hours, such that the product obtained will contain the desired number of moles of the monounsaturated carboxylic reactant per mole of the halogenated backbones. Alternatively, the backbone and the monounsaturated carboxylic reactant are mixed and heated while adding chlorine to the hot material.

The hydrocarbon or polymer backbone can be functionalized, e.g., with carboxylic acid producing moieties (preferably acid or anhydride moieties) selectively at sites of carbon-to-carbon unsaturation on the polymer or hydrocarbon chains, or randomly along chains using the three processes mentioned above or combinations thereof in any sequence.

The preferred monounsaturated reactants that are used to functionalize the backbone comprise mono- and dicarboxylic acid material, i.e., acid, anhydride, or acid ester material, including (i) monounsaturated $C_4$ to $C_{10}$ dicarboxylic acid wherein (a) the carboxyl groups are vicinyl, (i.e., located on adjacent carbon atoms) and (b) at least one, preferably both, of said adjacent carbon atoms are part of said mono unsaturation; (ii) derivatives of (i) such as anhydrides or $C_1$ to $C_5$ alcohol derived mono- or diesters of (i); (iii) monounsaturated $C_3$ to $C_{10}$ monocarboxylic acid wherein the carbon-carbon double bond is conjugated with the carboxy group, i.e., of the structure —C=C—CO—; and (iv) derivatives of (iii) such as $C_1$ to $C_5$ alcohol derived mono- or diesters of (iii). Mixtures of monounsaturated carboxylic materials (i)–(iv) also may be used. Upon reaction with the backbone, the monounsaturation of the monounsaturated carboxylic reactant becomes saturated. Thus, for example, maleic anhydride becomes backbone-substituted succinic anhydride, and acrylic acid becomes backbone-substituted propionic acid. Exemplary of such monounsaturated carboxylic reactants are fumaric acid, itaconic acid, maleic acid, maleic anhydride, chloromaleic acid, chloromaleic anhydride, acrylic acid, methacrylic acid, crotonic acid, cinnamic acid, and lower alkyl (e.g., $C_1$ to $C_4$ alkyl) acid esters of the foregoing, e.g., methyl maleate, ethyl fumarate, and methyl fumarate. The monounsaturated carboxylic reactant, preferably maleic anhydride, typically will be used in an amount ranging from about 0.01 to about 20 wt. %, preferably 0.5 to 10 wt. %, based on the weight of the polymer or hydrocarbon.

While chlorination normally helps increase the reactivity of starting olefin polymers with monounsaturated functionalizing reactant, it is not necessary with the polymers or hydrocarbons contemplated for use in the present invention, particularly those preferred polymers or hydrocarbons which possess a high terminal bond content and reactivity. Preferably, therefore, the backbone and the monounsaturated functionality reactant, e.g., carboxylic reactant, are contacted at elevated temperature to cause an initial thermal "ene" reaction to take place. Ene reactions are known.

The hydrocarbon or polymer backbone can be functionalized by random attachment of functional moieties along the polymer chains by a variety of methods. For example, the polymer, in solution or in solid form, may be grafted with the monounsaturated carboxylic reactant, as described above, in the presence of a free-radical initiator. When performed in solution, the grafting takes place at an elevated temperature in the range of about 100 to 260° C., preferably 120 to 240° C. Preferably, free-radical initiated grafting would be accomplished in a mineral lubricating oil solution containing, e.g., 1 to 50 wt. %, preferably 5 to 30 wt. % polymer based on the initial total oil solution.

The free-radical initiators that may be used are peroxides, hydroperoxides, and azo compounds, preferably those that have a boiling point greater than about 100° C. and decompose thermally within the grafting temperature range to provide free-radicals. Representative of these free-radical initiators are azobutyronitrile, 2,5-dimethylhex-3-ene-2,5-bis-tertiary-butyl peroxide and dicumene peroxide. The initiator, when used, typically is used in an amount of between 0.005% and 1% by weight based on the weight of the reaction mixture solution. Typically, the aforesaid monounsaturated carboxylic reactant material and free-radical initiator are used in a weight ratio range of from about 1.0:1 to 30:1, preferably 3:1 to 6:1. The grafting is preferably carried out in an inert atmosphere, such as under nitrogen blanketing. The resulting grafted polymer is characterized by having carboxylic acid (or ester or anhydride) moieties randomly attached along the polymer chains: it being understood, of course, that some of the polymer chains remain ungrafted. The free radical grafting described above can be used for the other polymers and hydrocarbons of the present invention.

The functionalized oil-soluble polymeric hydrocarbon backbone may then be further derivatized with a nucleophilic reactant, such as an amine, amino-alcohol, alcohol, metal compound, or mixture thereof, to form a corresponding derivative. Useful amine compounds for derivatizing functionalized polymers comprise at least one amine and can comprise one or more additional amine or other reactive or polar groups. These amines may be hydrocarbyl amines or may be predominantly hydrocarbyl amines in which the hydrocarbyl group includes other groups, e.g., hydroxy groups, alkoxy groups, amide groups, nitriles, imidazoline groups, and the like. Particularly useful amine compounds include mono- and polyamines, e.g., polyalkene and polyoxyalkylene polyamines of about 2 to 60, such as 2 to 40 (e.g., 3 to 20) total carbon atoms having about 1 to 12, such as 3 to 12, and preferably 3 to 9 nitrogen atoms per molecule. Mixtures of amine compounds may advantageously be used, such as those prepared by reaction of alkylene dihalide with ammonia. Preferred amines are aliphatic saturated amines, including, for example, 1,2-diaminoethane; 1,3-diaminopropane; 1,4-diaminobutane; 1,6-diaminohexane; polyethylene amines such as diethylene triamine; triethylene tetramine; tetraethylene pentamine; and polypropyleneamines such as 1,2-propylene diamine; and di-(1,2-propylene) triamine.

Other useful amine compounds include: alicyclic diamines such as 1,4-di(aminomethyl) cyclohexane and heterocyclic nitrogen compounds such as imidazolines.

Another useful class of amines is the polyamido and related amido-amines as disclosed in U.S. Pat. Nos. 4,857,217; 4,956,107; 4,963,275; and 5,229,022. Also usable is tris (hydroxymethyl)amino methane (TAM) as described in U.S. Pat. Nos. 4,102,798; 4,113,639; 4,116,876; and UK 989,409. Dendrimers, star-like amines, and comb-structured amines may also be used. Similarly, one may use condensed amines, as described in U.S. Pat. No. 5,053,152. The functionalized polymer is reacted with the amine compound using conventional techniques as described, for example, in U.S. Pat. Nos. 4,234,435 and 5,229,022, as well as in EP-A-208,560.

The functionalized, oil-soluble polymeric hydrocarbon backbones may also be derivatized with hydroxy compounds such as monohydric and polyhydric alcohols, or with aromatic compounds such as phenols and naphthols. Preferred polyhydric alcohols include alkylene glycols in which the alkylene radical contains from 2 to 8 carbon atoms. Other useful polyhydric alcohols include glycerol, monooleate of glycerol, monostearate of glycerol, monomethyl ether of glycerol, pentaerythritol, dipentaerythritol, and mixtures thereof. An ester dispersant may also be derived from unsaturated alcohols, such as allyl alcohol, cinnamyl alcohol, propargyl alcohol, 1-cyclohexane-3-ol, and oleyl alcohol. Still other classes of alcohols capable of yielding ashless dispersants comprise ether-alcohols, including oxy-alkylene and oxy-arylene. Such ether-alcohols are exemplified by ether-alcohols having up to 150 oxy-alkylene radicals in which the alkylene radical contains from 1 to 8 carbon atoms. The ester dispersants may be di-esters of succinic acids or acid-esters, i.e., partially esterified succinic acids, as well as partially esterified polyhydric alcohols or phenols, i.e., esters having free alcohols or phenolic hydroxy radicals. An ester dispersant may be prepared by any one of several known methods as described, for example, in U.S. Pat. No. 3,381,022.

Preferred groups of dispersant include polyamine-derivatized poly α-olefin, dispersants, particularly ethylene/butene alpha-olefin and polyisobutylene-based dispersants. Particularly preferred are ashless dispersants derived from polyisobutylene substituted with succinic anhydride groups and reacted with polyethylene amines, e.g., polyethylene diamine, tetraethylene pentamine; or a polyoxyalkylene polyamine, e.g., polyoxypropylene diamine, trimethylolaminomethane; a hydroxy compound, e.g., pentaerythritol; and combinations thereof. One particularly preferred dispersant combination is a combination of (A) polyisobutylene substituted with succinic anhydride groups and reacted with (B) a hydroxy compound, e.g., pentaerythritol; (C) a polyoxyalkylene polyamine, e.g., polyoxypropylene diamine, or (D) a polyalkylene diamine, e.g., polyethylene diamine and tetraethylene pentamine using about 0.3 to about 2 moles of (B), (C) and/or (D) per mole of (A). Another preferred dispersant combination comprises a combination of (A) polyisobutenyl succinic anhydride with (B) a polyalkylene polyamine, e.g., tetraethylene pentamine, and (C) a polyhydric alcohol or polyhydroxy-substituted aliphatic primary amine, e.g., pentaerythritol or trismethylolaminomethane, as described in U.S. Pat. No. 3,632,511.

Another class of high molecular weight ashless dispersants comprises Mannich base condensation products. Generally, these products are prepared by condensing about one mole of a long chain alkyl-substituted mono- or polyhydroxy benzene with about 1 to 2.5 moles of carbonyl compound(s) (e.g., formaldehyde and paraformaldehyde) and about 0.5 to 2 moles of polyalkylene polyamine, as disclosed, for example, in U.S. Pat. No. 3,442,808. Such Mannich base condensation products may include a polymer product of a metallocene catalyzed polymerization as a substituent on the benzene group, or may be reacted with a compound containing such a polymer substituted on a succinic anhydride in a manner similar to that described in U.S. Pat. No. 3,442,808. Examples of functionalized and/or derivatized olefin polymers synthesized using metallocene catalyst systems are described in the publications identified supra.

The high molecular weight dispersant can be further post treated by a variety of conventional post treatments such as boration, as generally taught in U.S. Pat. Nos. 3,087,936 and 3,254,025. Boration of the dispersant is readily accomplished by treating an acyl nitrogen-containing dispersant with a boron compound such as boron oxide, boron halide boron acids, and esters of boron acids, in an amount sufficient to provide from about 0.1 to about 20 atomic proportions of boron for each mole of acylated nitrogen composition. Useful dispersants contain from about 0.05 to about 2.0 wt. %, e.g., from about 0.05 to about 0.7 wt. % boron. The boron, which appears in the product as dehydrated boric acid polymers (primarily $(HBO_2)_3$), is believed to attach to the dispersant imides and diimides as amine salts, e.g., the metaborate salt of the diimide. Boration can be carried out by adding from about 0.5 to 4 wt. %, e.g., from about 1 to about 3 wt. % (based on the weight of acyl nitrogen compound) of a boron compound, preferably boric acid, usually as a slurry, to the acyl nitrogen compound and heating with stirring at from about 135° C. to about 190° C., e.g., 140° C. to 170° C., for from about 1 to about 5 hours, followed by nitrogen stripping. Alternatively, the boron treatment can be conducted by adding boric acid to a hot reaction mixture of the dicarboxylic acid material and amine, while removing water. Other post reaction processes known in the art can also be applied.

Conventional high molecular weight dispersants, in addition to providing sludge dispersing properties, also imbue lubricating oils with soot dispersancy characteristics. Surprisingly, it has been found that the Mannich Base condensation products of the present invention synergistically boost the soot dispersancy properties of high molecular weight dispersants. Thus, the use of a small amount of the Mannich Base condensation products of the present invention allows one to reduce the amount of the relatively expensive high molecular weight dispersant used in the lubricating oil composition while maintaining, or actually increasing, the soot dispersant properties of the composition. To provide sufficient control of soot induced viscosity increase, a conventional lubricating oil composition will employ a high molecular weight dispersant in an amount of up to about 20 wt. %, more usually up to about 8 wt. %, based on the total mass of the finished lubricant. In contrast, in a lubricating oil composition containing about 0.01 to about 5 wt. %, preferably from about 0.05 to about 2 wt. %, more preferably from about 0.1 to about 1 wt. %, of a Mannich Base condensation product of the present invention, a comparable level of sludge and soot dispersancy can be achieved with about 1 to about 12 wt. %, preferably from about 1 to about 7 wt. %, more preferably from about 2 to about 5 wt. %, of the high molecular weight dispersant. In general, each 0.5 wt. % increase in the amount of the Mannich base condensation product of the present invention may allow for up to a 5 wt. % reduction in the amount of needed high molecular weight dispersant.

Additional additives may be incorporated in the compositions of the invention to enable them to meet particular requirements. Examples of additives which may be included in the lubricating oil compositions of the present invention are detergents, metal rust inhibitors, viscosity index improvers, corrosion inhibitors, oxidation inhibitors, friction modifiers, anti-foaming agents, anti-wear agents and pour point depressants. Some are discussed in further detail below.

Metal-containing or ash-forming detergents function both as detergents to reduce or remove deposits and as acid neutralizers or rust inhibitors, thereby reducing wear and corrosion and extending engine life. Detergents generally comprise a polar head with a long hydrophobic tail, with the polar head comprising a metal salt of an acidic organic compound. The salts may contain a substantially stoichiometric amount of the metal in which case they are usually described as normal or neutral salts, and would typically have a total base number or TBN (as can be measured by ASTM D2896) of from 0 to 80. A large amount of a metal base may be incorporated by reacting excess metal compound (e.g., an oxide or hydroxide) with an acidic gas (e.g., carbon dioxide). The resulting overbased detergent comprises neutralized detergent as the outer layer of a metal base (e.g. carbonate) micelle. Such overbased detergents may have a TBN of 150 or greater, and typically will have a TBN of from 250 to 450 or more.

Detergents that may be used include oil-soluble neutral and overbased sulfonates, phenates, sulfurized phenates, thiophosphonates, salicylates, and naphthenates and other oil-soluble carboxylates of a metal, particularly the alkali or alkaline earth metals, e.g., sodium, potassium, lithium, calcium, and magnesium. The most commonly used metals are calcium and magnesium, which may both be present in detergents used in a lubricant, and mixtures of calcium and/or magnesium with sodium. Particularly convenient metal detergents are neutral and overbased calcium sulfonates having TBN of from 20 to 450 TBN, and neutral and overbased calcium phenates and sulfurized phenates having TBN of from 50 to 450. Combinations of detergents, whether overbased or neutral or both, may be used.

Sulfonates may be prepared from sulfonic acids which are typically obtained by the sulfonation of alkyl substituted aromatic hydrocarbons such as those obtained from the fractionation of petroleum or by the alkylation of aromatic hydrocarbons. Examples included those obtained by alkylating benzene, toluene, xylene, naphthalene, diphenyl or their halogen derivatives such as chlorobenzene, chlorotoluene and chloronaphthalene. The alkylation may be carried out in the presence of a catalyst with alkylating agents having from about 3 to more than 70 carbon atoms. The alkylaryl sulfonates usually contain from about 9 to about 80 or more carbon atoms, preferably from about 16 to about 60 carbon atoms per alkyl substituted aromatic moiety.

The oil soluble sulfonates or alkaryl sulfonic acids may be neutralized with oxides, hydroxides, alkoxides, carbonates, carboxylate, sulfides, hydrosulfides, nitrates, borates and ethers of the metal. The amount of metal compound is chosen having regard to the desired TBN of the final product but typically ranges from about 100 to 220 wt. % (preferably at least 125 wt. %) of that stoichiometrically required.

Metal salts of phenols and sulfurized phenols are prepared by reaction with an appropriate metal compound such as an oxide or hydroxide and neutral or overbased products may be obtained by methods well known in the art. Sulfurized phenols may be prepared by reacting a phenol with sulfur or a sulfur containing compound such as hydrogen sulfide, sulfur monohalide or sulfur dihalide, to form products which are generally mixtures of compounds in which 2 or more phenols are bridged by sulfur containing bridges.

Dihydrocarbyl dithiophosphate metal salts are frequently used as antiwear and antioxidant agents. The metal may be an alkali or alkaline earth metal, or aluminum, lead, tin, molybdenum, manganese, nickel or copper. The zinc salts are most commonly used in lubricating oil in amounts of 0.1 to 10, preferably 0.2 to 2 wt. %, based upon the total weight of the lubricating oil composition. They may be prepared in accordance with known techniques by first forming a dihydrocarbyl dithiophosphoric acid (DDPA), usually by reaction of one or more alcohol or a phenol with $P_2S_5$ and then neutralizing the formed DDPA with a zinc compound. For example, a dithiophosphoric acid may be made by reacting mixtures of primary and secondary alcohols. Alternatively, multiple dithiophosphoric acids can be prepared where the hydrocarbyl groups on one are entirely secondary in character and the hydrocarbyl groups on the others are entirely primary in character. To make the zinc salt, any basic or neutral zinc compound could be used but the oxides, hydroxides and carbonates are most generally employed. Commercial additives frequently contain an excess of zinc due to the use of an excess of the basic zinc compound in the neutralization reaction.

The preferred zinc dihydrocarbyl dithiophosphates are oil soluble salts of dihydrocarbyl dithiophosphoric acids and may be represented by the following formula:

wherein R and R' may be the same or different hydrocarbyl radicals containing from 1 to 18, preferably 2 to 12, carbon atoms and including radicals such as alkyl, alkenyl, aryl, arylalkyl, alkaryl and cycloaliphatic radicals. Particularly preferred as R and R' groups are alkyl groups of 2 to 8 carbon atoms. Thus, the radicals may, for example, be ethyl, n-propyl, i-propyl, n-butyl, i-butyl, sec-butyl, amyl, n-hexyl, i-hexyl, n-octyl, decyl, dodecyl, octadecyl, 2-ethylhexyl, phenyl, butylphenyl, cyclohexyl, methylcyclopentyl, propenyl, butenyl. In order to obtain oil solubility, the total number of carbon atoms (i.e. R and R') in the dithiophosphoric acid will generally be about 5 or greater. The zinc dihydrocarbyl dithiophosphate can therefore comprise zinc dialkyl dithiophosphates. The present invention may be particularly useful when used with lubricant compositions containing phosphorus levels of from about 0.02 to about 0.12 wt. %, preferably from about 0.03 to about 0.10 wt. %, more preferably from about 0.05 to about 0.08 wt. %, Oxidation inhibitors or antioxidants reduce the tendency of mineral oils to deteriorate in service. Oxidative deterioration can be evidenced by sludge in the lubricant, varnish-like deposits on the metal surfaces, and by viscosity growth. Such oxidation inhibitors include hindered phenols, alkaline earth metal salts of alkylphenolthioesters having preferably $C_5$ to $C_{12}$ alkyl side chains, calcium nonylphenol sulfide, oil soluble phenates and sulfurized phenates, phosphosulfurized or sulfurized hydrocarbons or esters, phosphorous esters, metal thiocarbamates, oil soluble copper compounds as described in U.S. Pat. No. 4,867,890, and molybdenum-containing compounds.

Aromatic amines having at least two aromatic groups attached directly to the nitrogen constitute another class of compounds that is frequently used for antioxidancy. While these materials may be used in small amounts, preferred embodiments of the present invention are free of these compounds. They are preferably used in only small amounts, i.e., up to 0.4 wt. %, or more preferably avoided altogether other than such amount as may result as an impurity from another component of the composition.

Typical oil soluble aromatic amines having at least two aromatic groups attached directly to one amine nitrogen contain from 6 to 16 carbon atoms. The amines may contain more than two aromatic groups. Compounds having a total of at least three aromatic groups in which two aromatic groups are linked by a covalent bond or by an atom or group (e.g., an oxygen or sulfur atom, or a —CO—, —SO$_2$— or alkylene group) and two are directly attached to one amine nitrogen also considered aromatic amines having at least two aromatic groups attached directly to the nitrogen. The aromatic rings are typically substituted by one or more substituents selected from alkyl, cycloalkyl, alkoxy, aryloxy, acyl, acylamino, hydroxy, and nitro groups. The amount of any such oil soluble aromatic amines having at least two aromatic groups attached directly to one amine nitrogen should preferably not exceed 0.4 wt. % active ingredient.

Representative examples of suitable viscosity modifiers are polyisobutylene, copolymers of ethylene and propylene, polymethacrylates, methacrylate copolymers, copolymers of an unsaturated dicarboxylic acid and a vinyl compound, interpolymers of styrene and acrylic esters, and partially hydrogenated copolymers of styrene/isoprene, styrene/butadiene, and isoprene/butadiene, as well as the partially hydrogenated homopolymers of butadiene and isoprene.

Friction modifiers and fuel economy agents that are compatible with the other ingredients of the final oil may also be included. Examples of such materials include glyceryl monoesters of higher fatty acids, for example, glyceryl mono-oleate; esters of long chain polycarboxylic acids with diols, for example, the butane diol ester of a dimerized unsaturated fatty acid; oxazoline compounds; and alkoxylated alkyl-substituted mono-amines, diamines and alkyl ether amines, for example, ethoxylated tallow amine and ethoxylated tallow ether amine.

A viscosity index improver dispersant functions both as a viscosity index improver and as a dispersant. Examples of viscosity index improver dispersants include reaction products of amines, for example polyamines, with a hydrocarbyl-substituted mono- or dicarboxylic acid in which the hydrocarbyl substituent comprises a chain of sufficient length to impart viscosity index improving properties to the compounds. In general, the viscosity index improver dispersant may be, for example, a polymer of a $C_4$ to $C_{24}$ unsaturated ester of vinyl alcohol or a $C_3$ to $C_{10}$ unsaturated monocarboxylic acid or a $C_4$ to $C_{10}$ di-carboxylic acid with an unsaturated nitrogen-containing monomer having 4 to 20 carbon atoms; a polymer of a $C_2$ to $C_{20}$ olefin with an unsaturated $C_3$ to $C_{10}$ mono- or di-carboxylic acid neutralized with an amine, hydroxyamine or an alcohol; or a polymer of ethylene with a $C_3$ to $C_{20}$ olefin further reacted either by grafting a $C_4$ to $C_{20}$ unsaturated nitrogen-containing monomer thereon or by grafting an unsaturated acid onto the polymer backbone and then reacting carboxylic acid groups of the grafted acid with an amine, hydroxy amine or alcohol.

Pour point depressants, otherwise known as lube oil flow improvers (LOFI), lower the minimum temperature at which the fluid will flow or can be poured. Such additives are well known. Typical of those additives that improve the low temperature fluidity of the fluid are $C_8$ to $C_{18}$ dialkyl fumarate/vinyl acetate copolymers, and polymethacrylates. Foam control can be provided by an antifoamant of the polysiloxane type, for example, silicone oil or polydimethyl siloxane.

Some of the above-mentioned additives can provide a multiplicity of effects; thus for example, a single additive may act as a dispersant-oxidation inhibitor. This approach is well known and need not be further elaborated herein.

In the present invention it may be necessary to include an additive which maintains the stability of the viscosity of the blend. Thus, although polar group-containing additives achieve a suitably low viscosity in the pre-blending stage it has been observed that some compositions increase in viscosity when stored for prolonged periods. Additives which are effective in controlling this viscosity increase include the long chain hydrocarbons functionalized by reaction with mono- or dicarboxylic acids or anhydrides which are used in the preparation of the ashless dispersants as hereinbefore disclosed.

When lubricating compositions contain one or more of the above-mentioned additives, each additive is typically blended into the base oil in an amount that enables the additive to provide its desired function.

It may be desirable, although not essential, to prepare one or more additive concentrates comprising additives (concentrates sometimes being referred to as additive packages) whereby several additives can be added simultaneously to the oil to form the lubricating oil composition. The final composition may employ from 5 to 25 mass %, preferably 5 to 18 mass %, typically 10 to 15 mass % of the concentrate, the remainder being oil of lubricating viscosity.

When lubricating compositions contain one or more of the above-mentioned additives, each additive is typically blended into the base oil in an amount that enables the additive to provide its desired function. Representative effect amounts of such additives, when used in crankcase lubricant, are listed below. All the values listed are stated as mass percent active ingredient.

| ADDITIVE | MASS % (Broad) | MASS % (Preferred) |
|---|---|---|
| Metal Detergents | 0.1–15 | 0.2–9 |
| Corrosion Inhibitor | 0–5 | 0–1.5 |
| Metal Dihydrocarbyl Dithiophosphate | 0.1–6 | 0.1–4 |
| Antioxidant | 0–5 | 0.01–2 |
| Pour Point Depressant | 0.01–5 | 0.01–1.5 |
| Antifoaming Agent | 0–5 | 0.001–0.15 |
| Supplemental Antiwear Agents | 0–1.0 | 0–0.5 |
| Friction Modifier | 0–5 | 0–1.5 |
| Viscosity Modifier | 0.01–10 | 0.25–3 |
| Basestock | Balance | Balance |

All weight percents expressed herein (unless otherwise indicated) are based on active ingredient (A.I.) content of the additive, and/or upon the total weight of any additive-package, or formulation which will be the sum of the A.I. weight of each additive plus the weight of total oil or diluent.

This invention will be further understood by reference to the following examples, wherein all parts are parts by weight, unless otherwise noted and which include preferred embodiments of the invention.

SYNTHESIS EXAMPLE A

Synthesis of alpha-naphthol-2HT Mannich Base Condensation Product 50 g (0.347 mol) of alpha-naphtol were added to a 1 liter four necked round bottomed flask equipped with an air stirrer, thermometer and nitrogen blanket. About 100 ml. of toluene (other neutral solvents such as heptane or a neutral diluent oil could also be used) were added and the mixture was stirred at room temperature while adding 347 g (0.694 mol) of hydrogenated di-tallow amine, commonly referred to as 2HT amine. The reaction mixture was then heated to 50° C. and 60 g (0.72 mol) of formalin (37% formaldehyde) was introduced. Thereafter, the toluene solution was heated to 90° C. and soaked at this temperature for 2 hours. The reaction mixture was then heated slowly to 150° C. while distilling off the water and toluene. Once the water was distilled off, the residue was stripped at 150° C. with nitrogen until constant weight. The product was collected and solidified while cooling to room temperature. Analytical results indicated that the product contained 2.44% nitrogen. $C^{13}$ NMR showed the product as having a di-substituted structure substituted at the ortho/para position relative to the hydroxy group with an average of 1.5 to 1.7 sidechains per naphthol ring.

SYNTHESIS EXAMPLE B

Synthesis of alkylated alpha-naphthol with 1-octadecene 50 g (0.347 mol) of alpha-naphthol were charged into a reactor containing 175 g (0.694 mol) of 1-octadecene. While stirring under a nitrogen blanket, 100 g of dry Amberlyst 15 were added and the reaction mixture was heated to 110° C. for 9 hours. The product was diluted with 100 ml of heptane and filtered. The solvent was nitrogen stripped, and the residue was vacuum stripped at 200° C. until constant weight to insure that the unreacted olefin was removed. The product analyzed to be greater than 95% active ingredient. GC analysis showed that the product was a mixture of mono- and di-substituted naphthol with about 1.7 alkyl chains per naphthol ring. C-13 and proton analysis indicated that the alkyl-substituted napthol was primarily ortho/para alkylated naphthol.

SYNTHESIS EXAMPLE C

Synthesis of alpha-naphthol-di-coco amine Mannich Base Condensation Product 20.59 g (0.0143 mol) of alpha-naphthol were added to a 1 liter four necked round bottomed flask equipped with an air stirrer, thermometer, and nitrogen blanket containing 125.2 g of mineral oil Solvent 100 Neutral, FN 1365. Then, 100.96 g (0.286 mol) of di-coco amine, commercially sold as Adogen-260, were added and the mixture was stirred while heating to 80° C. At 80° C., 25.51 g (0.315 mol) of formalin (37% formaldehyde) were added slowly via an addition funnel. Thereafter, the reaction mixture was soaked at 80° C. for 2 hours. The reaction mixture was then heated slowly to 150° C. while distilling off the water and mineral oil. Once the water stopped distilling off, the residue was stripped at 150° C. with nitrogen until constant weight. A 50% oil solution product was collected. Analytical results show the product to contain 1.56% N. The FTIR spectrum of the product was identical to the spectrum of a product obtained when using toluene as the solvent.

SYNTHESIS EXAMPLE D

Synthesis of beta-naphthol Mannich Base Condensation Product 36 g (0.25 mol) of beta-naphthol were added to a 2 liter four necked round bottomed flask equipped with an air stirrer, thermometer, and nitrogen blanket containing 500 ml of heptane. Then, 250 g (0.50 mol) of 2HT amine were added and the mixture was stirred while heating to 80° C. At 80° C., 45 g (0.55 mol) of formalin (37% formaldehyde) were added slowly via an addition funnel. Thereafter, the reaction mixture was soaked at 80° C. for 2 hours. The reaction mixture was then heated slowly to 150° C. while distilling the water and heptane. Once the water stopped distilling off, the residue was stripped at 150° C. with nitrogen until constant weight. The product was collected and solidified while cooling to room temperature. FTIR spectrum and $C^{13}$ and proton NMR indicates that the desired product was provided

SYNTHESIS EXAMPLE E

Synthesis of alkylated alpha naphthol with 1-octadecene 50 g (0.347 mol) of alpha-naphthol were charged into a reactor containing 175 g (0.694 mol) of 1-octadecene. While stirring under a nitrogen blanket, 100 g of dry Amberlyst 15 were added and the reaction mixture heated to 110° C. for 9 hours. The product was diluted with 100 ml of heptane and filtered. The solvent was nitrogen stripped and the residue was vacuum stripped at 200° C. until constant weight to insure that the unreacted olefin was stripped. The product analyzed to be greater than 95% active ingredient. GC analysis shows the product to be a mixture of mono- and di-substituted naphthol, with about 1.7 chains per naphthol ring. $C^{13}$ and proton NMR analysis showed the product to be primarily ortho/para-alkylated naphthol.

SYNTHESIS EXAMPLE F

Synthesis of Phenol-2HT Mannich Base, (Phe/Formalin/2HT=1.0/1.0/1.1)

28.2 g (0.30 mol) of phenol were added to a 250 ml four necked round bottomed flask equipped with an air stirrer, thermometer, and nitrogen blanket containing 100 ml of heptane. Then, 150 g (0.30 mol) of 2HT amine were added and the mixture was stirred while heating to 80° C. At 80° C., 26.75 g (0.33 mol) of formalin (37% formaldehyde) were added slowly via an addition funnel. Thereafter, the reaction mixture was soaked at 80° C. for 2 hours. The reaction mixture was then heated slowly to 150° C. while distilling the water and heptane. Once the water stopped distilling off, the residue was stripped at 150° C. with nitrogen until constant weight. The product was collected and solidified while cooling to room temperature. Analytical results show the product to contain 2.2% N. FTIR spectrum and $C^{13}$ and proton NMR indicated that the desired product was provided.

SYNTHESIS EXAMPLE G

Synthesis of Phenol-2HT Mannich Base, (Phe/Formalin/2HT=1.0/2.0/2.2)

18.8 g (0.20 mol) of phenol were added to a 250 ml four necked round bottomed flask equipped with an air stirrer, thermometer, and nitrogen blanket containing 100 ml of heptane. Then, 200 g (0.40 mol) of 2HT amine were added and the mixture was stirred while heating to 80° C. At 80° C., 35.7 g (0.44 mol) of formalin (37% formaldehyde) were added slowly via an addition funnel. Thereafter, the reaction mixture was soaked at 80° C. for 2 hours. The reaction mixture was then heated slowly to 150° C. while distilling the water and heptane. Once the water stopped distilling off, the residue was stripped at 150° C. with nitrogen until constant weight. The product was collected and solidified while cooling to room temperature. Analytical results show the product to contain 2.49 N. FTIR spectrum and $C^{13}$ and proton NMR indicates that the desired product was provided.

SYNTHESIS EXAMPLE H

Synthesis of Phenol-2HT Mannich Base, (Phe/Formalin/2HT=1.0/3.0/3.3)

14.1 g (0.15 mol) of phenol were added to a 250 ml four necked round bottomed flask equipped with an air stirrer, thermometer, and nitrogen blanket containing 100 ml of heptane. Then, 225 g (0.45 mol) of 2HT amine were added and the mixture was stirred while heating to 80° C. At 80° C., 40.1 g (0.49 mol) of formalin (37% formaldehyde) were added slowly via an addition funnel. Thereafter, the reaction mixture was soaked at 80° C. for 2 hours. The reaction mixture was then heated slowly to 150° C. while distilling the water and heptane. Once the water stopped distilling off, the residue was stripped at 150° C. with nitrogen until constant weight. The product was collected and solidified while cooling to room temperature. Analytical results showed the product to contain 2.60 N. FTIR spectrum and $C^{13}$ and proton NMR analysis indicated that the desired product was provided.

SYNTHESIS EXAMPLE I

Synthesis of alpha-napthoxazine (alpha-napthol/formalin/oleyl amine=1:2:1)

144 g (1 mol) of solid alpha-napthol was charged into a four-neck reaction flask equipped with mechanical stirrer, thermometer, Dean Stark trap with a water condenser, and nitrogen blanket. 200 ml of methanol was added to dissolve the α-naphthol at room temperature. Slowly, 276 g (1 mol) of oleyl amine (Armeen OL; Akzo Nobel) were added while stirring under nitrogen blanket. No exothermal observed during the addition of the amine to the alpha-naphthol-methanol solution. While stirring at about 20° C., 162.2 g (2 mol) of formalin (37 wt % solution of formaldehyde in water) were slowly added. The reaction is exothermic and the reaction temperature was maintained below 25–30° C. by cooling the reactor with an outside ice water bath and by controlling the formalin addition. Once the formalin was added and the exothermal reaction ceased, the reaction mixture was allowed to warm to room temperature. The temperature of the reaction mixture was slowly increased up to 90° C. while the methanol and water distilled out. Nitrogen flow was increased to strip the remaining water in the product at about 100° C. until all the water is removed. Vacuum could have been applied instead of nitrogen stripping. The naphthoxazine analyzed for 3.23% N (3.22 theory).

SYNTHESIS EXAMPLE J

Synthesis of beta-napthoxazine (beta-napthol/formalin/oleyl amine=1:2:1)

144 g (1 mol) of solid beta-napthol was charged into a four-neck reaction flask equipped with mechanical stirrer, thermometer, Dean Stark trap with a water condenser, and nitrogen blanket. 200 ml of methanol was added to dissolve the β-naphthol at room temperature. Slowly, 276 g (1 mol) of oleyl amine (Armeen OL; Akzo Nobel) were added while stirring under nitrogen blanket. No exothermal observed during the addition of the amine to the beta-naphthol-methanol solution. While stirring at about 20° C., 162.2 g (2 mol) of formalin (37 wt % solution of formaldehyde in water) were slowly added. The reaction is exothermic and the reaction temperature was maintained below 25–30° C. by cooling the reactor with an outside ice water bath and by controlling the formalin addition. Once the formalin was added and the exothermal reaction ceased, the reaction mixture was allowed to warm to room temperature. The temperature of the reaction mixture was slowly increased up to 90° C. while the methanol and water distilled out. Nitrogen flow was increased to strip the remaining water in the product at about 100° C. until all the water is removed. Vacuum could have been applied instead of nitrogen stripping. The naphthoxazine analyzed for 3.23% N (3.22 theory).

Product Performance

The ability of a composition to control soot-induced viscosity increase, and thus, the ability of a composition to maintain soot in suspension, can be measured using bench tests including the carbon black bench test (CBBT) and Haake Carbon Black Test. Procedures for performing these tests are industry standard and well known, but are summarized below:

Carbon Black Bench Test (CBBT)

In the carbon black bench tests performed in association herewith, a compound of the present invention (as a dispersant booster) and a primary, high molecular weight dispersant are blended into a simplified oil formulation containing the dispersant mixture, a detergent, antioxidant, and antiwear agent. The components of the oil formulation are subjected to an initial blending procedure. Carbon black, as a surrogate for soot, is added to the oil. The dispersion is mixed in a high-speed blender, followed by stirring to ensure proper mixing of the carbon black into the oil. The kinematic viscosity is then measured in a cross-arm tube at 100° C. Lower viscosity with respect to the appropriate control indicates better soot dispersancy.

Haake Carbon Black Test

The Haake Carbon Black Test involves blending the dispersant into a formulated oil. In the tests conducted in association herewith, the tested formulation contains a high molecular weight dispersant and a compound of the present invention together with detergent, viscosity modifier, antioxidant and antiwear agent. The components of the oil formulation are subjected to an initial blending. Carbon black powder is then added to a final concentration and the sample is blended overnight. The viscosity of the carbon black dispersion is then measured in a Haake rheometer over a range of shear rates from 0.1 $sec^{-1}$ to 30 $sec^{-1}$. Typically, the viscosity at shear rates 0.26 $sec^{-1}$ and 0.45 $sec^{-1}$ are used for comparison.

EXAMPLE 1

Lubricating oil formulations were formed by blending into a base oil, for 1 hour at 70° C., constant amounts of detergent, antioxidant and antiwear agent and variable amounts of a high molecular weight dispersant (a PIBSA-PAM product derived from PIBSA having a number average molecular weight of about 2200, and having a succination ratio of about 1.1), and a compound of the present invention (alpha-napthol 2HT). The formulations were subjected to carbon black bench testing (CBBT) wherein carbon black was blended into the formulations at variable concentrations. The carbon black was added to the oil in the form of a 20% paste in basestock, to reduce flyaway dust and was dispersed into the formulation by blending using a high speed blender for 5 minutes, followed by stirring for 90 minutes at 100° C. The kinematic viscosity of the formulation was then measured in a cross-arm tube at 100° C.

Figure 1:
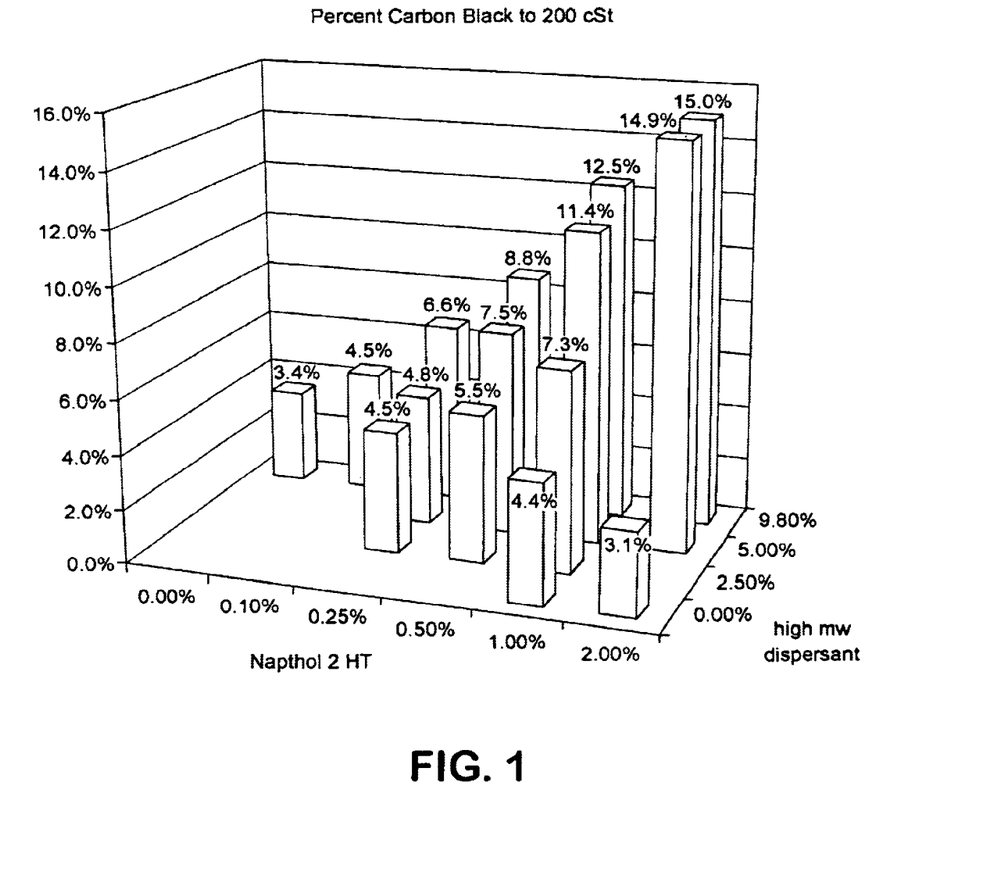
FIG. 1 illustrates graphically the synergistic effect on the soot handling capacity, as measured using a carbon black bench test, of lubricating oil compositions containing a combination of a compound of the invention and a conventional high molecular weight dispersant, compared to lubricating oil compositions containing comparable amounts of either a compound of the invention or a conventional high molecular weight dispersant.

The results achieved are shown in the 3-D plot of FIG. 1. As shown by FIG. 1, the Mannich base condensation products of the present invention act as potent soot dispersancy boosters when used in combination with high molecular weight dispersants. For example, a formulated oil containing 9.8 wt. % of the high molecular weight dispersant and none of the Mannich base condensation product of the present invention is shown to reach a kinematic viscosity of 200 cSt at a soot content of only 3.4%. In contrast, a formulation containing the same amount of the high molecular weigh dispersant, but further containing only 0.50% of the Mannich base condensation product of the present invention does not reach a viscosity of 200 cSt until the soot content reaches 8.8%. When 2% of the Mannich base condensation product of the present invention is provided, a viscosity of 200 cSt is not reached until the soot level is 15%.

EXAMPLE 2

Lubricating oil formulations were formed by blending into a base oil (Mobil 700N) for 1 hour at 100° C., constant amounts of detergent, antioxidant and antiwear agent and variable amounts of a high molecular weight dispersant (a PIBSA-PAM product derived from PIBSA having a number average molecular weight of about 2200 and having a succination ratio of about 1.1), and naphthoxazine compounds of the present invention. 4.76 wt. % of carbon black was blended into each of the formulations overnight at 90° C. The kinematic viscosity of each of the resulting carbon black dispersions was then measured in a Haake rheometer over a range of shear rates from 0.1 sec$^{-1}$ to 0.45 sec$^{-1}$. As is typical, the viscosity at shear rates of 0.26 sec$^{-1}$ and 0.45 sec$^{-1}$ were used for comparison.

Figure 2:
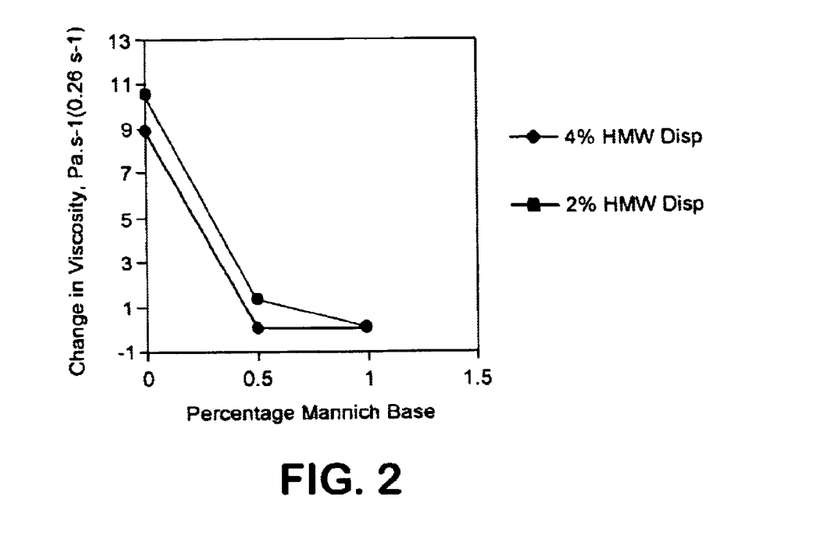
FIG. 2 illustrates graphically the reduction in soot-induced viscosity increase, as measured using a Haake carbon black test, of lubricating oils containing a combination of a compound of the invention (2HT-naphtol) and a conventional high molecular weight dispersant.

The comparative results of the Haake carbon black test are shown in FIG. 2. As shown by the data of FIG. 2, in formulations containing both 4% and 2% (AI) of high molecular weight dispersant, soot-induced viscosity increases are substantially eliminated when the oil formulation further contains from 0.5 to 1 wt. % of the Mannich base condensation product of the present invention.

EXAMPLE 3

Lubricating oil formulations were formed by blending into a base oil (Mobil 700N) for 1 hour at 100° C., constant amounts of detergent, antioxidant and antiwear agent and variable amounts of a high molecular weight dispersant (a PIBSA-PAM product derived from PIBSA having a number average molecular weight of about 2200 and having a succination ratio of about 1.1), and a compound of the present invention (alpha-napthol 2HT). 4.76 wt. % of carbon black was blended into each of the formulations overnight at 90° C. The kinematic viscosity of each of the resulting carbon black dispersions was then measured in a Haake rheometer over a range of shear rates from 0.1 sec$^{-1}$ to 0.45 sec$^{-1}$. As is typical, the viscosity at shear rates of 0.26 sec$^{-1}$ and 0.45 sec$^{-1}$ were used for comparison.

The comparative results of the Haake carbon black test are shown below in Table 1. As shown by the data of Table 1, in formulations containing both 4% and 2% (AI) of high molecular weight dispersant, soot-induced viscosity increases are substantially eliminated when the oil formulation further contains from 0.5 to 1 wt. % of the naphthoxazine Mannich base condensation products of the present invention.

TABLE 1

|  | Disp. Concentration | Naphthoxazine Concentration | η (Vis, Pa-s) at 0.45 l/s | η (Vis, Pa-s) at 1.25 l/s |
|---|---|---|---|---|
| Dispersant | 4 wt % | 0 | 4.17 | 1.54 |
|  | 2 wt % | 0 | 6.95 | 3.13 |
| β-Naphthoxazine | 2 wt % | 0.25 wt % | 7.08 | 3.19 |
|  | 2 wt % | 0.50 wt % | 3.24 | 1.19 |
|  | 2 wt % | 1.00 wt % | 2.98 | 1.10 |
| α-naphthoxazine | 2 wt % | 0.25 wt % | 0.042 | 0.035 |
|  | 2 wt % | 0.50 wt % | 0.083 | 0.048 |
|  | 2 wt % | 1.0 wt % | 0.064 | 0.049 |

As shown by the data of Table 1, in formulations containing both 4% and 2% (AI) of high molecular weight dispersant, soot-induced viscosity increases are substantially eliminated when the oil formulation further contains from 0.5 to 1 wt. % of the naphtoxazine Mannich base condensation products of the present invention.

EXAMPLE 4

Figure 3:
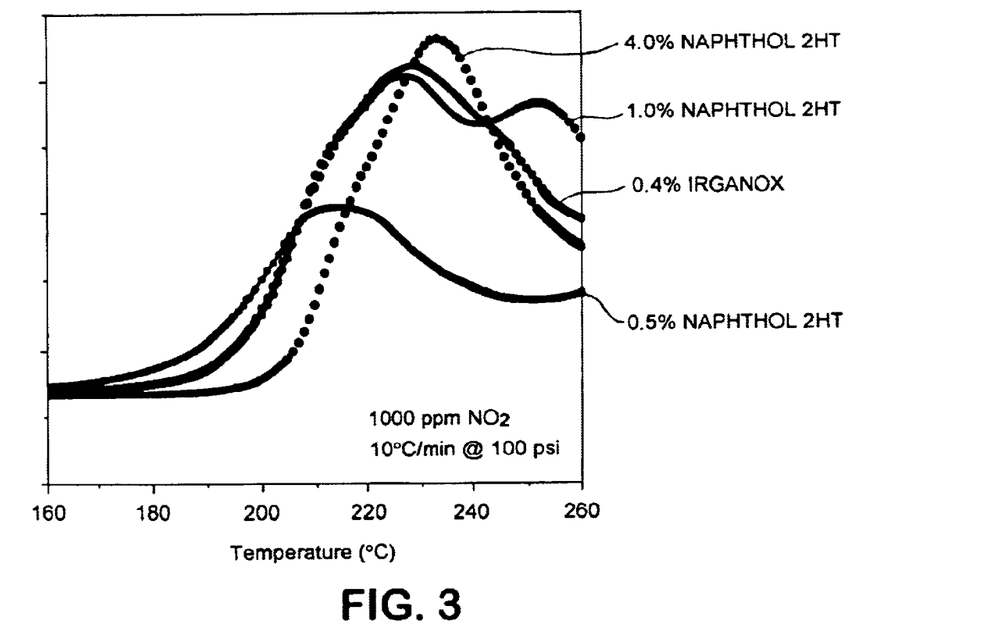
FIG. 3 illustrates graphically the antioxidancy properties of a compound of the invention compared to a commercially available antioxidant.

The efficacy of a Naphthol Mannich base product of the present invention as an antioxidant was determined relative to a commercial antioxidant (Irganox L135, Ciba Specialty Chemicals) by NOxidation test using High Pressure Scanning Calorimetric measurements. As shown in FIG. 3, an increase in concentration of Naphtol-2HT Mannich base increases the oil stability in $NO_2$ and, at comparable treat rates, the antioxidancy effect of the compound of the present invention was similar to that of Irganox L135.

The disclosures of all patents, articles and other materials described herein are hereby incorporated, in their entirety, into this specification by reference. The principles, preferred embodiments and modes of operation of the present invention have been described in the foregoing specification. What applicants submit is their invention, however, is not to be construed as limited to the particular embodiments disclosed, since the disclosed embodiments are regarded as illustrative rather than limiting. Changes may be made by those skilled in the art without departing from the spirit of the invention.

What is claimed is:

1. A compound of the general formula (I):

wherein:

Ar is a polynuclear aromatic moiety;

$R_1$ and $R_2$ are independently selected from H and $C_1$–$C_{30}$ straight or branched chain hydrocarbyl groups optionally containing one or more hetero atoms selected from N, O and S;

$R_3$ is a straight or branched chain hydrocarbyl group;

$R_4$ is H or a $C_1$ to $C_9$ straight or branched chain hydrocarbyl group;

q is 1 or 2;

x is 1 to 3;

y is from 1 to 2 times the number of aromatic rings in Ar; and z is zero to a number equal to the number of remaining substitutable hydrogens on aromatic moiety Ar;

wherein a hydroxyl group attached to Ar combines with N—R$_1$ to form a substituted or unsubstituted 6 membered oxazine ring, provided that, when z is 0, R$_2$ is not H.

2. A compound of claim 1, wherein Ar is selected from bi-phenyl, naphthyl, bi-naphthyl, pyrene, chrysene, anthracene, phenanthracine, fluorene and indene.

3. A compound of claim 2, wherein Ar is naphthyl.

4. An oxazine ring-containing condensation product of (a) a polynuclear hydroxyaromatic compound optionally substituted with hydrocarbyl; (b) a C$_1$–C$_{10}$ aldehyde; and (c) an amine containing from 1 to 60 carbon atoms and from 1 to 12 nitrogen atoms per molecule.

5. A product of claim 4, wherein said polynuclear aromatic moiety is selected from wherein Ar is selected from bi-phenyl, naphthyl, bi-naphthyl, pyrene, chrysene, anthracene, phenanthracine, fluorene and indene.

6. A product of claim 5, wherein said polynuclear aromatic moiety is naphthyl.

7. A lubricating oil composition comprising a major amount of oil of lubricating viscosity and a minor amount of at least one compound of the general formula (I):

(I)

wherein:

Ar is mono- or polynuclear aromatic moiety;

R$_1$ and R$_2$ are independently selected from H and C$_1$–C$_{30}$ straight or branched chain hydrocarbyl groups optionally containing one or more hetero atoms selected from N, O and S;

R$_3$ is a straight or branched chain hydrocarbyl group;

R$_4$ is H or a C$_1$ to C$_9$ straight or branched chain hydrocarbyl group;

q is 1 or 2;

x is 1 to 3;

y is from 1 to 2 times the number of aromatic rings in Ar; and z is zero to a number equal to the number of remaining substitutable hydrogens on aromatic moiety Ar; wherein a hydroxyl group attached to Ar combines with N—R$_1$ to form a substituted or unsubstituted 6 membered oxazine ring, provided that, when z is 0, R$_2$ is not H.

8. A lubricating oil composition of claim 7 comprising from about 0.01 to 10 wt. % of said compound, based on the total weight of said composition.

9. A lubricating oil composition of claim 8 comprising from about 0.1 to about 1 wt. % of said compound, based on the total weight of said composition.

10. A lubricating oil composition of claim 7, further comprising a minor amount of at least one high molecular weight dispersant.

11. A lubricating oil composition of claim 10 comprising from about 0.01 to about 5 wt. %, based on the total weight of said composition, of said compound, and from about 1 to about 12 wt. %, based on the total weight of said composition, of said high molecular weight dispersant.

12. A lubricating oil composition of claim 11 comprising from about 0.1 to about 2 wt. %, based on the total weight of said composition, of said compound, and from about 2 to about 5 wt. %, based on the total weight of said composition, of said high molecular weight dispersant.

13. A lubricating oil composition of claim 7 wherein Ar of said compound is a polynuclear aromatic moiety.

14. A lubricating oil composition of claim 13, wherein Ar is selected from bi-phenyl, naphthyl, bi-naphthyl, pyrene, chrysene, anthracene, phenanthracine, fluorene and indene.

15. A lubricating oil composition of claim 14, wherein Ar is naphthyl.

* * * * *